US006528293B1

United States Patent
Nakajima et al.

(10) Patent No.: US 6,528,293 B1
(45) Date of Patent: Mar. 4, 2003

(54) METHOD OF PRODUCING ACTIVATED LIPASE

(75) Inventors: Mitsutoshi Nakajima, Ibaraki (JP); Hiroshi Nabetani, Ibaraki (JP); Sosaku Ichikawa, Ibaraki (JP); Minoru Seki, Tokyo (JP); Tatsuo Maruyama, Ibaraki (JP)

(73) Assignees: Japan as represented by Director of National Food Research Institute, Ibaraki (JP); Ministry of Agriculture, Forestry and Fisheries, Tokyo (JP); Bio-Oriented Technology Research Advancement Institution

( * ) Notice: Subject to any disclaimer, the term of this patent is extended or adjusted under 35 U.S.C. 154(b) by 0 days.

(21) Appl. No.: 09/415,924

(22) Filed: Oct. 12, 1999

(30) Foreign Application Priority Data

Mar. 24, 1999 (JP) ............................................. 11-078861

(51) Int. Cl.⁷ ........................... C12N 9/00; C12N 11/02; C12N 9/96; C12N 9/20
(52) U.S. Cl. ....................... 435/183; 435/177; 435/188; 435/198
(58) Field of Search ................................ 435/177, 183, 435/198, 188

(56) References Cited

U.S. PATENT DOCUMENTS

| 4,011,169 | A | * | 3/1977 | Diehl et al. | .................... 252/95 |
| 5,219,733 | A | * | 6/1993 | Myojo et al. | ................. 435/52 |
| 5,856,163 | A | * | 1/1999 | Hashida et al. | ............. 435/198 |

FOREIGN PATENT DOCUMENTS

JP          61149084       *   7/1986

* cited by examiner

*Primary Examiner*—Jon P. Weber
*Assistant Examiner*—Kailash C. Srivastava
(74) *Attorney, Agent, or Firm*—Carrier, Blackman & Associates, P.C.; Joseph P. Carrier; William D. Blackman

(57) ABSTRACT

A method is disclosed for activating a lipase by adding a solution of lipase in an aqueous buffer at a pH near neutrality to an organic phase, e.g., tetradecane. Under these conditions lipase is activated as a function of an organic-and-water boundary surface between the organic and water phases. The lipase that is activated in this manner remains active even after lyophilization to remove the water and the organic phase. This activated lipase efficiently catalyzes a fat reforming reaction in non-aqueous and nano-aqueous conditions.

8 Claims, 4 Drawing Sheets

(a)  (b)

(a)

(b)

METHOD OF PRODUCING ACTIVATED LIPASE

BACKGROUND OF THE INVENTION

1. Field of the Invention

The present invention relates to a method of activating of an enzyme such as lipase, etc., to reaction of such activated enzyme including reformation of fat, and further to a method of deactivating the enzyme once it is activated.

2. Description of Related Art

Conventionally, the production of many useful products has been achieved with use of enzymes. In particular, lipase was widely used for reforming fat so as to produce edible oil, soap, glycerin, dairy or milk products, etc., because of the versatility thereof.

Today where resources, energy, and ecological problems are discussed daily on a global scale, many expectations are applied to efficient and safe production of important materials (i.e., fatty acids, etc.) in the chemical industry, as well as to high-performance materials to which much attention is paid in the fields of pharmaceuticals and foodstuffs, with the use of the enzyme which can be represented by lipase.

As a method for obtaining a target material with use of the enzyme, there can be listed a hydrolysis reaction with use of lipase, transesterification, and ester synthesis or composing reaction, etc.

As a different method for reforming those fats, conventionally, an organic synthetic method using high temperature is mainly used or practiced. However, such method cannot be applied to materials which are unstable at high temperatures, and it is impossible to reproduce the target material with high efficiency due to poor enatioselectivity. Further, with the enzyme method but not with the organic synthetic method, since a residual activating material which may have toxicity or may cause a side reaction is used for increasing the activity of the enzyme, a problem arises in particular in the field of foodstuffs.

Therefore, production of the useful materials by catalytic reaction with use of an enzyme with high efficiency and with safety is considered.

For example, in a case of the catalytic reaction with use of lipase, it was reported that it proceeds with the useful enatioselectivity where 1-phenylethylelaurate (R-soma) is synthesized on a basis of 1-phenylethanol and lauric acid, as the ester synthesis between fatty acid and asymmetric alcohol.

Also, aside from the enatioselectivity, if the lipase having selectivity in a reacting portion, in particular participating in ester bonding between a first order ($1^{st}$ order) and a third order ($3^{rd}$ order) of triglyceride is used, it is possible to put the target fatty acid into the positions of only the first and the third orders. However, in a case of a chemical method using an inorganic catalyst, there is no such selectivity, therefore the fatty acid is put in at random.

However, most enzymes, such as lipase, show only a hydrolysis reaction in water solution, and will not proceed to the reaction if a powder thereof is simply dispersed into an organic solvent by itself.

Then, for conducting the transesterification and the ester composing reaction, which are industrially valuable, with high efficiency in a non-aqueous or nano-aqueous system or condition, there are proposed various methods, including a method in which the enzyme is fixed onto a carrier, a method in which the surface the enzyme is made hydrophobic with a covalent bond, and a method which the enzyme is modified with a surfactant or fatty acid.

For fixing the enzyme onto the carrier, there are already known a method in which the enzyme is physically absorbed onto the surface of an inorganic carrier, such as alumina particles, and a method in which the enzyme is fixed with the covalent bond onto the surface of latex particles or silica particles.

For making the surface of the enzyme hydrophobic, there is already known a method in which polyethylene glycol is bonded on the surface of the enzyme with the covalent bond, and there is also known a method in which the enzyme is made soluble into an organic solvent.

Further, for modifying the lipase (i.e., the enzyme) with the fatty acid or the surfactant, there is known a method in which the enzyme is bonded with the fatty acid or the surfactant through an interaction which seems to be electrostatic, hydrophilic or hydrophobic.

With the method of fixing the enzyme onto the carrier, however, it is impossible to conduct the transesterification or the ester composing reaction with such high efficiency. Further, there results a solid enzyme which cannot be applied to the production of foodstuffs.

With the method of making the surface of an enzyme hydrophobic, however, the enzyme is easily deactivated during the process of making it hydrophobic, and the activity which can be actually obtained therefrom is low. The chemical(s) used for making the surface of the enzyme hydrophobic cannot be used for producing the foodstuffs, thereby restricting the utilization of the enzyme itself.

With the method of modifying the enzyme with the fatty acid and/or the surfactant, the enzyme shows interesterification activity under the condition where it forms a compound with the fatty acid and/or the surfactant. However the enzyme itself does not show the activity. In other words, since it is impossible to remove the modification(s) of the fatty acid and/or the surfactant from a reaction system, there is a probability that the fatty acid and/or the surfactant may participate in some kind reaction so that the modification is mixed or added into a product or a secondary product.

SUMMARY OF THE INVENTION

It is considered that lipase has an active site and a "lid" covering the active site, and it is low in interesterification activity under the condition where the lid is closed as shown in FIG. 1($a$), while high in interesterification activity under the condition where the lid is open as shown in FIG. 1($b$).

The lipase is considered to close the lid thereof in water solution so that it is in the condition where a substrate (i.e., water) cannot enter into the active site. However, in a water solution mixed with fat, it is considered that the lipase gathering on a boundary surface between water and fat opens the lid thereof so as to accelerate the hydrolysis reaction. By the way, the above consideration can be confirmed by the fact that hydrolysis is increased rapidly by a fat concentration exceeding a level of saturation of fat.

As mentioned previously, the reaction will not occur even if the powder of lipase is dispersed into the organic solvent. However, the lipase being modified with the fatty acid shows the activity of the enzyme in the organic solvent.

This is inferred by the inventors, as shown in FIG. 2, because the hydrophobic portion of the lipase enters into double layers of fat being approximately 5 nm in the thickness thereof, while the hydrophilic portion thereof forms a compound protruding from double layers of fat.

According to the present invention, upon the above inference, it is considered that the enzyme should show the activity thereof if it is kept with the lid open in the non-aqueous or nano-aqueous system, where no boundary surface exists with a water phase, thereby accomplishing the present invention.

Namely, according to the present invention, there is provided a method for producing activated enzyme, comprising the following steps:

adding enzyme to water and fat phases of a multi-phase system;

activating the enzyme due to a function of a fat-and-water boundary surface between the water and fat phases; and removing the water and fat phases while maintaining an activated condition of the enzyme.

As a concrete method for adding the enzyme into the two-phase system of the water phase and the fat phase, there can be considered a method of adding the fat phase to a water solution into which the enzyme has been dissolved in advance.

And, as a means for removing the fat phase and the water phase while keeping the activating condition of the enzyme, freeze-drying (or lyophilization) is appropriate.

Further, a concrete example of the enzyme can be listed as lipase, and as the fat phase can be listed a volatile one, such as tetradecane.

Further, when activating, the pH of the water phase (buffer solution) is preferably maintained in a vicinity of neutrality, and the addition amount of said tetradecane is to be from 1% to 10% of the volume of the buffer solution.

By contacting the activated enzyme obtained from the method according to the present invention described above with fat in non-aqueous system or nano-aqueous system, reforming can be conducted, such as transesterification reaction, ester composing reaction, etc.

Further, in a method for inactivating an activated enzyme, according to the present invention, the activated enzyme, which is activated by means of the above method or the other method(s), is dispersed and stirred into a buffer solution in which there exists no boundary surface between fat and water.

BRIEF DESCRIPTION OF DRAWINGS

FIG. 1(a) is a block diagram of showing lipase being in a not-active condition, while FIG. 1(b) shows it being in the active condition;

DETAIL DESCRIPTION OF THE PREFERRED EMBODIMENTS

Hereinafter, detailed explanation of the embodiments according to the present invention will be given by referring to the attached drawings. As used herein, the language "fat phase" is used interchangeably with "organic phase" and "organic solvents".

Lipase (20 mg originated from Rhizopus japonicus) is dissolved into buffer solution (5 ml), and into the obtained water solution is added tetradecan] $C_{14}H_{30}$ as fatty phase.

After stirring at 40° C. for one (1) hour under the condition of two-phases of the tetradecan $C_{14}H_{30}$ and the buffer solution, the lipase is freeze dried, whereby water and fat are removed therefrom.

With use of such a lipase as obtained in this manner, transesterification reaction is conducted between stearic acid and tripalmitin in hexane.

Figure 1:
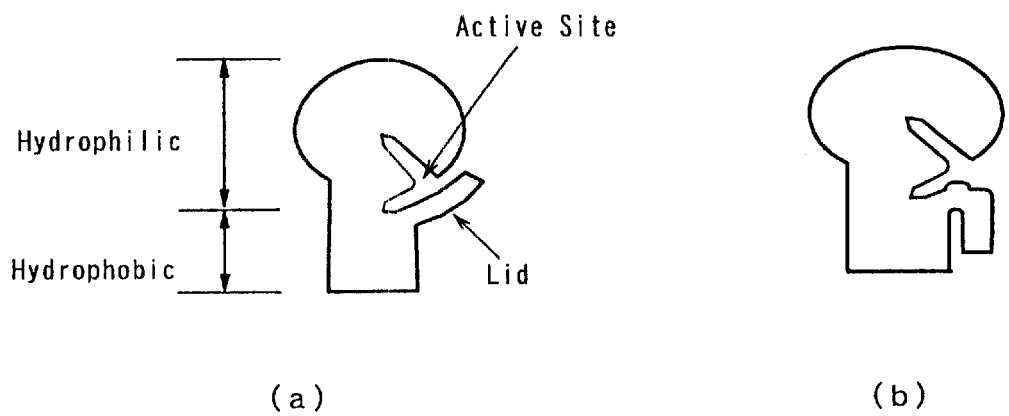
Figure 2:
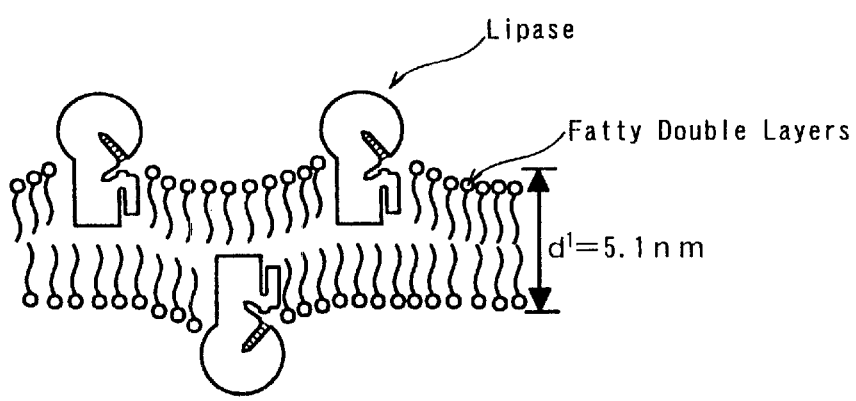
FIG. 2 is a block diagram of lipase compound being modified with fatty acid.
Figure 3:
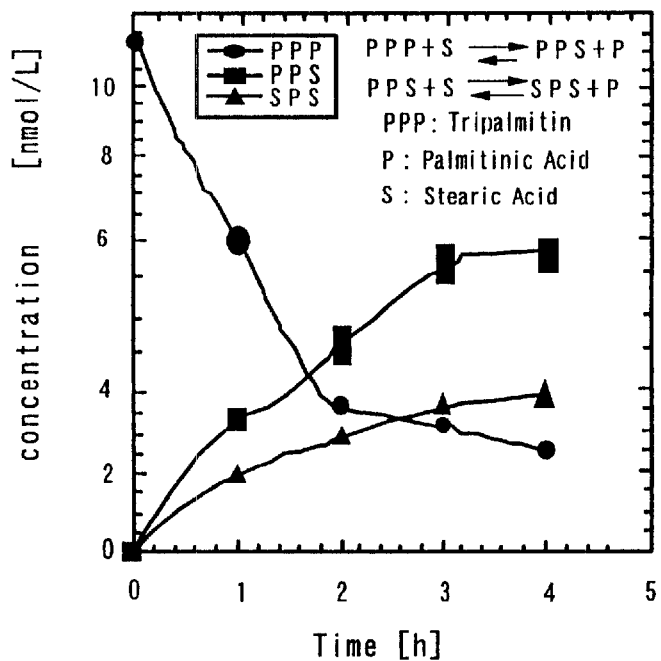
FIG. 3 is a graph showing a relationship between a concentration of product through transesterification between stearic acid and tripalmitin, with respect to time.

In the graph of FIG. 3, there is shown a relationship between elapsed time of the transesterification reaction between stearic acid and tripalmitin and product formed thereby.

As is apparent from FIG. 3, it can be seen that the lipase which has not shown catalytic activity in organic solvent until now begins to show the catalytic activity remarkably.

On the other hand, if the powdered lipase without this operation is used under the same condition, such a reaction will not proceed at all. Namely, it is apparent that the lipase can show the activity in the organic solvent, when it is freeze-dried from the buffer solution under the existence of the tetradecan.

Figure 4:
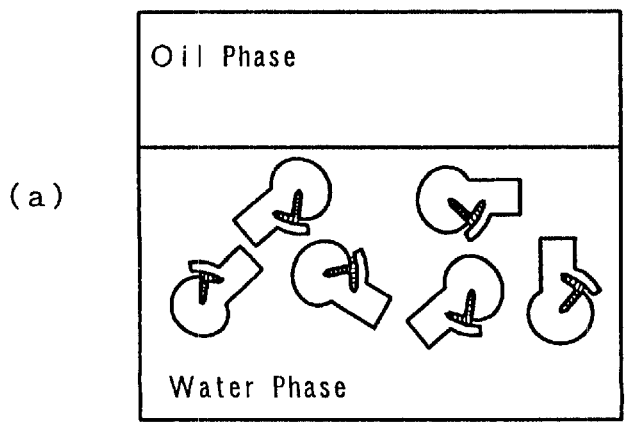
FIGS. 4(a) and (b) are views showing behavior of the lipase in a two-phase system.
Figure 4:
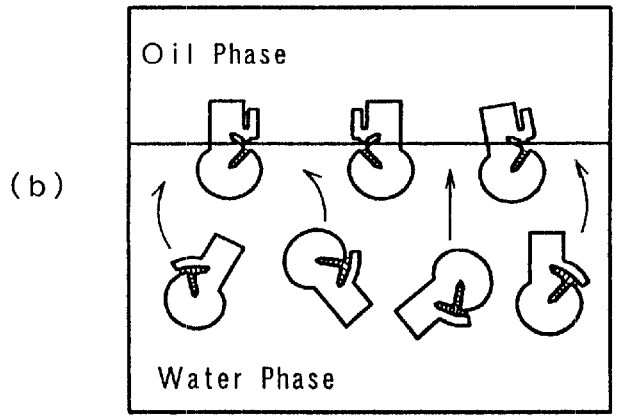

As the reason of showing the activity in the organic solvent in this manner, it can be considered that, just after adding the tetradecan into water phase into which the lipase is dissolved, as shown in FIG. 4(a), although there exists the lipase in the water phase, if there is a boundary surface between the water phase and the fat phase, the lipase moves towards the boundary surface since it has a tendency to gather around the boundary surface. The lipase, having moved to the boundary surface, has a hydrophobic portion at the side of the fat phase while having a hydrophilic portion at the side of the water phase, as shown in FIG. 4(b), and at the same time the lid covering over the activating portion is opened by the function of the boundary surface. It is also considered that this condition is maintained even if the lipase is freeze-dried.

(Kinds of Fat Phase)

Figure 5:
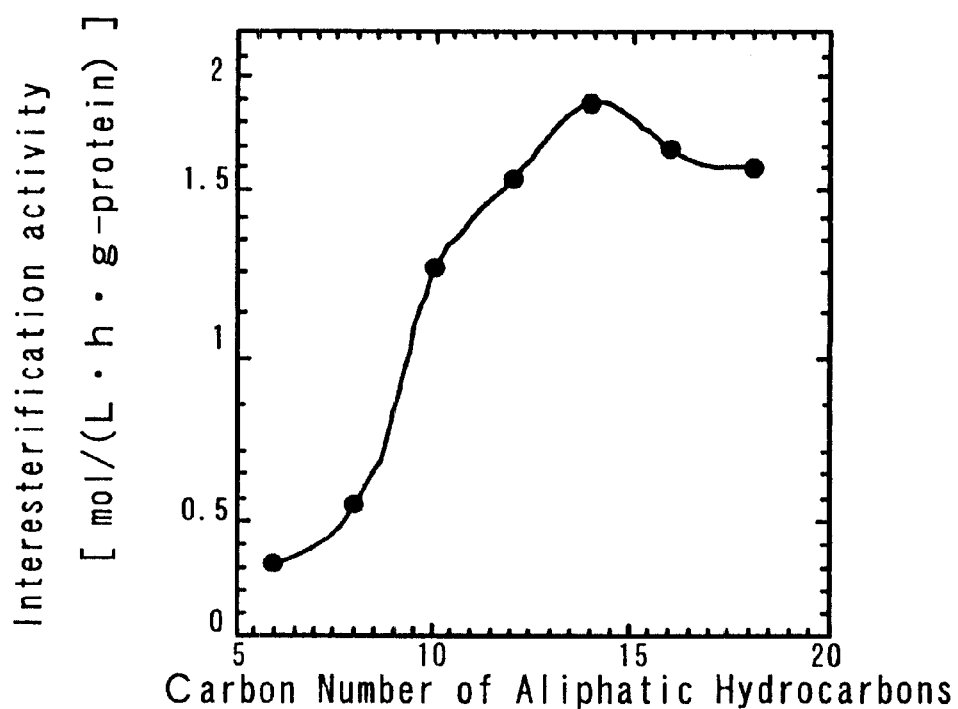
FIG. 5 is a graph showing a relationship between interesterification activity of lipase and the carbon number of a straight chain saturated hydrocarbon constituting a fat phase.

With use of various straight chain saturated hydrocarbons in place of the tetradecan, the activation of the lipase is tried under the same conditions as in the above. The result is shown in FIG. 5. The straight chain saturated hydrocarbons include hexane, octane, decane, dodecane, hexadecane, and octadecane other than the tetradecan.

As is apparent from FIG. 5, the highest activity is shown in a case where the tetradecan is used as the fat phase. This is because much of the lipase has a substrate specificity, and the substrate specificity is mainly determined by the lid of the lipase. Therefore, there exists the fat phase being suitable for opening the lid of the lipase, and it can be said that the tetradecan is the fat phase being most suitable among those hydrocarbons.

(Influences of pH)

Figure 6:
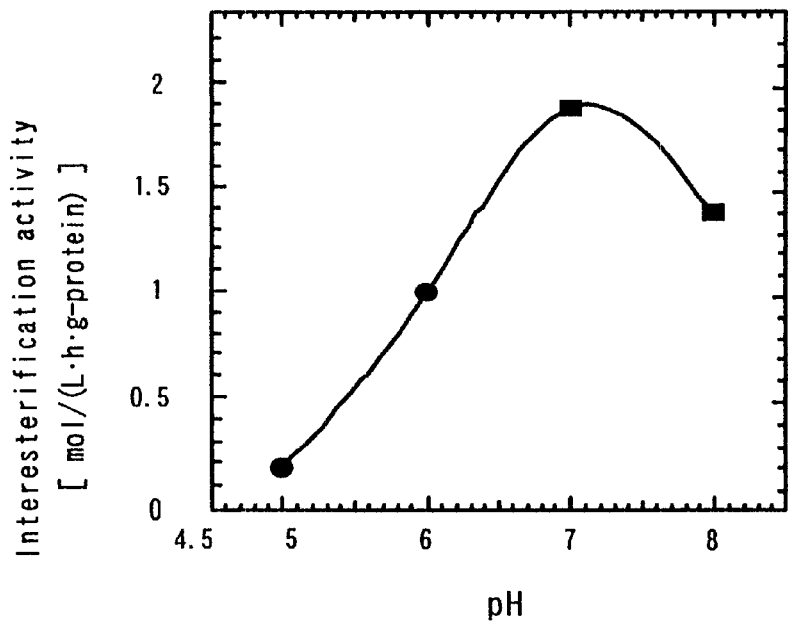
FIG. 6 is a graph showing a relationship between interesterification activity of lipase and pH of buffer solution.

The result of testing of the influence on the activation of the lipase by the pH of the buffer solution when treating a contact process on the boundary surface between fat and water is indicated on the graph in FIG. 6. In this graph, the buffer solution shows the highest activity in a case where the buffer solution is in the vicinity of neutrality (pH 7).

Figure 7:
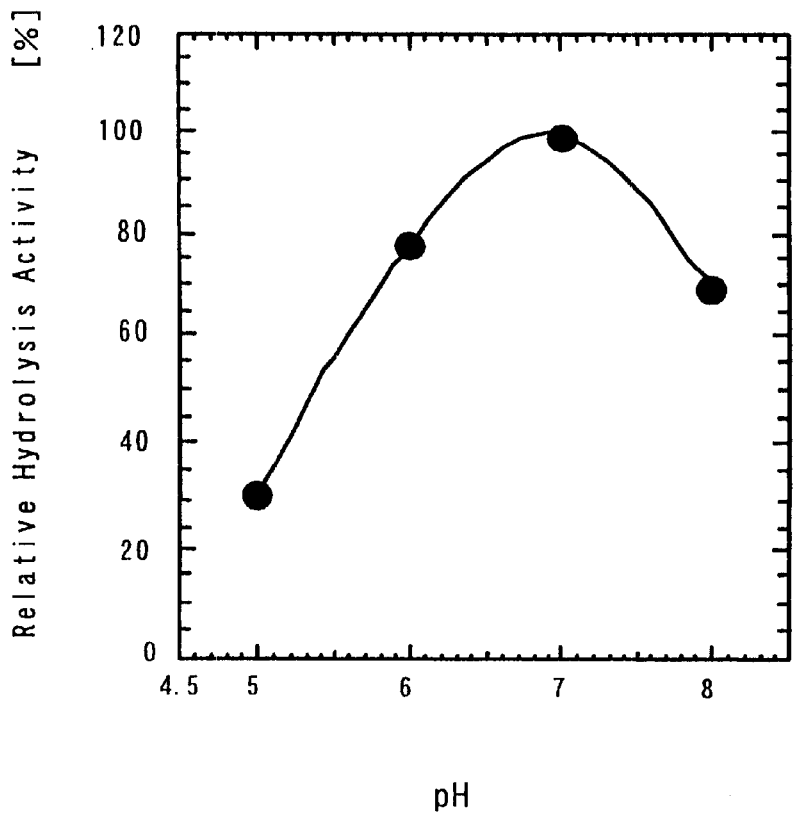
FIG. 7 is a graph showing a relationship between relative hydrolysis activity of lipase and pH.

On the other hand, the testing result of a relationship between relative hydrolysis activity of native crude lipase and the pH is indicated on the graph in FIG. 7.

The graphs shown in FIGS. 6 and 7 are similar to each other. This seems to indicate that a dissociation condition of remaining amino acid radicals at pH 7 is necessary for the lipase to show the catalytic activity.

(Amount of Fat Phase)

The amount of tetradecan with respect to the buffer solution (5 ml) is changed in a range from 1% (50 μL) to 10% (500 μL). As the result, there can be obtained catalytic activity being same as or similar to the case where the addition amount mentioned above is 5% (250 μL).

(Inactivation and Reactivation)

If the activation of the lipase by the contact processing on the boundary surface between fat and water mentioned above is caused by the fact that the lipase opens the lid, it is considered that the lid can also be closed, and the following experimentation was conducted.

First of all, treating the contact processing on the boundary surface between fat and water by the tetradecane, the activated lipase which has been freeze-dried is added with water so as to be dispersed in it again (since there remains original salt therein), and it is stirred at 4° C. for 24 hours. Thereafter, the activity of the dispersed lipase which is obtained by freeze-drying, in the organic solvent is investigated. As the result, it is determined that the lipase has returned back to the catalytic activity before the activation thereof.

Namely, it comes to be clear that the activated lipase can be easily deactivated by treating it in the buffer solution without the boundary surface between fat and water therein.

In this manner, if it can be deactivated temporarily and with ease, the enzyme can be deactivated freely when it should not participate the reaction during a series of synthetic reactions. Further, by controlling the deactivation and the re-activation of the enzyme, it is possible to proceed with the reactions in multi-steps or stages in the same reactor.

In the present embodiment, the enzyme is explained as lipase, however, for example, amylase and protease can also be activated on the boundary surface between water phase and fat phase.

As is explained in the above, according to the present invention, it is possible to obtain the activated enzyme (i.e., lipase) with a simple operation.

Further, since it is possible to obtain the enzyme activated individually without being reformed with other materials, no undesirable reaction caused by the reforming materials will occur nor will it be necessary to remove such reforming materials. Although there have been described what are the present embodiments of the invention, it will be understood that variations and modifications may be made thereto without departing from the gist, spirit, or essence of the invention. The scope of the invention is indicated by the appended claims.

What is claimed is:

1. A method for producing activated lipase, comprising the following steps:

combining a lipase, an organic phase and a water phase such that said lipase is activated by a function of an organic-and-water boundary surface between the organic and water phases; and treating said combined lipase, organic phase and water phase by removing the water and organic phases from the lipase while maintaining an activated condition of the lipase; and wherein the pH of said water phase is maintained in a vicinity of neutrality.

2. A method for producing activated lipase as defined in claim 1, wherein the step of adding the lipase to the water and organic phases is conducted by contacting the organic phase to a water solution into which the lipase is dissolved in advance.

3. A method for producing activated lipase as defined in claim 1, wherein said organic phase is volatile.

4. A method for producing activated lipase as defined in claim 1, wherein the removing step is conducted by freeze-drying.

5. A method for producing activated lipase as defined in claim 1, wherein said organic phase comprises tetradecane.

6. A method for producing activated lipase as defined in claim 5, wherein said water phase comprises a buffer solution, said step of combining said lipase, said organic phase and said water phase involves dissolving the lipase in the buffer solution and then adding the tetradecane thereto, and an addition amount of said tetradecan is selected to be from 1% to 10% of a volume of said buffer solution.

7. A method for producing activated lipase as defined in claim 1, wherein said activated lipase is capable of efficiently catalyzing a fat reforming reaction in non-aqueous and nano-aqueous systems.

8. A method for producing activated lipase as defined claim 1, wherein said lipase is from *Rhizopus japonicus*, and said organic phase comprises tetradecane.

* * * * *

UNITED STATES PATENT AND TRADEMARK OFFICE
CERTIFICATE OF CORRECTION

PATENT NO. : 6,528,293 B1
DATED : March 4, 2003
INVENTOR(S) : Mitsutoshi Nakajima et al.

It is certified that error appears in the above-identified patent and that said Letters Patent is hereby corrected as shown below:

Title page,
Item [73], Assignees, change "Ibaraki (JP); Ministry of Agriculture," to
-- Ministry of Agriculture, --; and
change "Forestry and Fisheries, Tokyo (JP);" to -- Forestry and Fisheries, Ibaraki (JP); --; and
after "Advancement Institution" insert -- Tokyo (JP) --.

Column 1,
Line 7, change "of activating of" to -- of activating --.
Line 8, after "such" insert -- an --.
Line 9, after "enzyme" insert a comma.
Line 35, between "method" and "but" insert a comma.
Line 67, after "surface" insert -- of --.

Column 2,
Line 1, after "method" insert -- in --.
Line 35, after "However" insert a comma.
Line 40, change "some kind reaction" to -- some kind of reaction --.
Line 67, before "double" insert -- the --.

Column 3,
Line 63, change "DETAIL" to -- DETAILED --.

Column 4,
Line 4, after "mg" insert a comma.
Line 6, change "tetradecan]" to -- tetradecane --.
Lines 8, 27, 30, 45, 49, 51 and 56, change "tetradecan" to -- tetradecane --.

Column 5,
Line 6, change "tetradecan" to -- tetradecane --.
Line 22, after "lipase" insert a comma.
Line 32, after "participate" insert -- in --.
Line 47, begin a new paragraph with -- Although --.

UNITED STATES PATENT AND TRADEMARK OFFICE
CERTIFICATE OF CORRECTION

PATENT NO. : 6,528,293 B1
DATED : March 4, 2003
INVENTOR(S) : Mitsutoshi Nakajima et al.

It is certified that error appears in the above-identified patent and that said Letters Patent is hereby corrected as shown below:

Column 6,
Line 37, change "tetradecan" to -- tetradecane --.
Line 43, after "defined" insert -- in --.

Signed and Sealed this

Twelfth Day of August, 2003

JAMES E. ROGAN
*Director of the United States Patent and Trademark Office*